United States Patent [19]

Hansen, Jr. et al.

[11] Patent Number: 4,722,922

[45] Date of Patent: * Feb. 2, 1988

[54] TETRAPEPTIDE AMIDES IN THE TREATMENT OF HYPERTENSION

[75] Inventors: Donald W. Hansen, Jr., Chicago; David A. Jones, Jr., Evanston; Robert H. Mazur, Chicago; James M. Schlatter, Glenview, all of Ill.

[73] Assignee: G. D. Searle & Co., Chicago, Ill.

[*] Notice: The portion of the term of this patent subsequent to Jan. 22, 2002 has been disclaimed.

[21] Appl. No.: 693,553

[22] Filed: Jan. 22, 1985

[51] Int. Cl.$^4$ ............................................. A61K 37/02
[52] U.S. Cl. ..................................................... 514/18
[58] Field of Search ........................................... 514/18

[56] References Cited

U.S. PATENT DOCUMENTS 4,495,178 1/1985 Hansen, Jr. et al. ......... 260/112.5 E
4,510,085 4/1985 Hansen, Jr. et al. ......... 260/112.5 E Primary Examiner—Donald B. Moyer
Assistant Examiner—F. T. Moezie
Attorney, Agent, or Firm—Mary Jo Kanady; Paul D. Matukaitis

[57] ABSTRACT

The invention relates to tetrapeptides of the formula I:

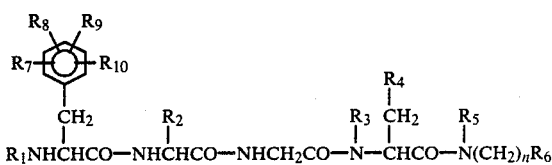

which are useful as renin inhibition/antihypertensive agents.

14 Claims, No Drawings

TETRAPEPTIDE AMIDES IN THE TREATMENT OF HYPERTENSION

BACKGROUND OF THE INVENTION

The present invention relates to tetrapeptide amides of Formula I which, surprisingly, have been found to possess renin inhibition properties and are thus useful in the treatment of hypertension.

Hypertension is a condition caused by any of a variety of functional abnormalities. For example, hypertension may be related to abnormalities in adrenergic, cholinergic, or neuromuscular interactions; in hormonal balance; or in kidney function, which malfunctions often are caused by abnormalities of the other systems. Treatment with drugs that are intended to act at some receptor site involved in one of the malfunctioning systems has frequently been the basis of therapy. For example, numerous neural receptor blockers are known to act as antihypertensive agents, and diuretics are commonly used to counteract the effects of fluid retention associated with kidney dysfunction. Each of these regimens, however, is associated with side effects often related to inadequate specificity. See generally L. S. Goodman and A. Gilman, eds. *The Pharmacological Basis of Therapeutics* (New York, 1975), Fifth Edition, Chaps. 26, 27, 28, 30, 33, 39, 40.

The renin-angiotensin system has been implicated in hypertension. See Goodman and Gilman, supra, pp. 630-637. The enzyme renin converts the plasma protein angiotensinogen to the essentially inactive decapeptide angiotensin I, which in turn is proteolytically converted by the so-called "converting enzyme" to the potently vasoactive octapeptide angiotensin II. Various peptidases further hydrolyze angiotensin II to essentially inactive peptide fragments. In addition to regulating blood pressure, angiotensin also stimulates the secretion of aldosterone and thus is intimately involved in regulating the sodium-potassium balance. Thus, inhibition of renin could be an important means of controlling high blood pressure. Certain short-chain peptide analogs of angiotensinogen segments have been reported to inhibit renin activity. K. Poulsen, J. Burton, and E. Haber, *Biochemistry*, 12, 3877-3882 (1973); J. Burton, K. Poulsen, and E. Haber, *Biochemistry*, 14, 3892-3898 (1975); J. Burton, R. J. Cody, Jr., A. J. Herd, and E. Haber, *Proc. Natl. Acad. Sci. U.S.A.*, 77, 5476-5479 (1980). Peptide inhibitors of renin activity have also been reported to lower blood pressure in primates. See J. Burton, R. J. Cody, Jr., A. J. Herd, and E. Haber, *Proc. Natl. Acad. Sci. U.S.A.*, 77, 5476-5479 (1980); R. J. Cody, J. Burton, G. Evin, K. Poulsen, J. A. Herd, and E. Haber, *Biochem. Biophys. Res. Commun.*, 97, 230-235 (1980). The present invention provides peptide amides of shorter length which are renin inhibitors and exhibit antihypertensive activity.

INFORMATION DISCLOSURE

U.S. Pat. No. 4,316,892 relates to certain derivatives of methionine enkephalin derivatives useful as analgesic agents. Also see Morgan U.S. Pat. No. 4,178,371 relating to analogous enkephalin type analgesics. Commonly assigned, allowed co-pending U.S. application Ser. No. 539,458, filed Oct. 6, 1983, claims enkephalin derivatives in which the amino acid in the fourth position is a hexahydrophenylalanine residue as being useful as analgesic agents. The foregoing application includes the statement that some of the compounds may have antihypertensive activity although no biological results are set forth. In contrast, the compounds of the present invention comprise those in which the amino acid residue in the fourth position is phenylalanine, or alkyl substituted phenylalanine derivatives.

SUMMARY OF THE INVENTION

The present invention particularly provides tetrapeptide amides according to Formula I.

$$R_1NHCHCO-NHCHCO-NHCH_2CO-N-CHCO-N(CH_2)_nR_6$$

with substituents: $CH_2$ (bearing $R_7, R_8, R_9, R_{10}$ on phenyl ring), $R_2$, $R_3$, $CH_2$ (bearing $R_4$ phenyl), $R_5$ wherein $R_1$ is:
(a) hydrogen; or
(b) alkyl of 1 to 6 carbon atoms, inclusive;

wherein $R_2$ is:
(a) alkyl of 1 to 6 carbon atoms, inclusive; or
(b)

$$-\underset{O_m}{CH_2CH_2SCH_3};$$

m being either zero, 1 or 2;

wherein $R_3$ is:
(a) hydrogen; or
(b) alkyl of 1 or 2 carbon atoms; inclusive;

wherein $R_4$ is:
(a) phenyl, optionally substituted by alkyl of 1 to 6 carbon atoms, inclusive:

wherein $R_5$ is:
(a) hydrogen; or
(b) alkyl of 1 to 6 carbon atoms, inclusive;

wherein $R_6$ is:
(a) carboxy;
(b) alkoxycarbonyl of 2 to 7 carbon atoms, inclusive;
(c) $CONH_2$;
(d) N,N-dialkylcarbamoyl of 3 to 7 carbon atoms, inclusive;
(e) hydroxy; or
(f) alkanoyloxy of 2 to 7 carbon atoms, inclusive;

wherein $R_7$, $R_8$, and $R_9$ are H or alkyl of 1 to 6 carbon atoms, and may be the same or different;

wherein $R_{10}$ is:
(a) hydrogen;
(b) hydroxy; or
(c) alkoxycarbonyloxy wherein the alkoxy portion is from 1 to 6 carbon atoms, inclusive;

wherein n is an integer of from 3 to 10 inclusive and the pharmocologically acceptable acid addition salts thereof.

Examples of alkoxy of one to six carbon atoms, inclusive, are methoxy, ethoxy, propoxy, butoxy, pentoxy, hexoxy, and the isomeric forms thereof.

Examples of alkyl of one to six carbon atoms inclusive, are methyl, ethyl, propyl, butyl, pentyl, and hexyl and the isomeric forms thereof.

The renin inhibition activity of the compounds of this invention illustrated in the examples was tested by the following method. Pepstatin and the octapeptide prolylhistidylprolylphenylalanylhistidylleucylphenylalanylvalyltyrosine (or, "Pro-[Phe⁶]octapeptide"; see J.

Burton, K. Poulsen, and E. Haber, *Biochemistry*, 14, 3892–3898 (1975)) are active in this assay.

Inhibition of Human Renin

International reference standard human renin, isolated from kidneys, was obtained from the World Health Organization International Laboratory for Biological Standards (National Institute for Biological Standards and Control, London, England). Renin activity is defined in "Goldblatt units" (GU), the quantity that, when injected directly into the blood stream of an unanesthetized dog, raises the direct mean femoral artery blood pressure by 30 mm Hg in about two minutes. E. Haas, L. Lewis, P. Scipione, and T. J. Koshy, *Hypertension*, 1, 112–117 (1979). Human angiotensinogen was used as an unisolated component of human blood plasma. The enzyme inhibition assay, see K. Poulsen, J. Burton, and E. Haber, *Biochemistry*, 12, 3877–3882 (1973), involved a two-hour incubation at 37° C. of the following final concentrations of reagents (0.25 ml total volume): 0.1 mGU/ml human renin; 0.05 ml human plasma; 6 mM disodium EDTA; 2.4 mM phenylmethylsulfonyl fluoride and 1.5 mM 8-hydroxyquinoline (angiotensinase inhibitors); 0.4 mg/ml bovine serum albumin; and 0.024 neomycin sulfate in 100 mM Tris-acetate buffer (pH 7.5). The enzymatic reaction was terminated by boiling the mixture for ten minutes. The quantity of angiotensin I formed was determined by radioimmunoassay, using the general method used in the angiotensin I radioimmunoassay kit of New England Nuclear. Test compounds were considered active if inhibition was greater than 20%.

The following tests further illustrate the in vivo methods for determining antihypertensive activity of the compounds of this invention.

Spontaneously Hypertensive Rat Assay—Indirect Measurement

Male spontaneously hypertensive rats were used in this assay. Initial systolic blood pressure was measured using a caudal plethysmograph immediately before administration of test compounds. For initial screening the test compounds were administered intragastrically at a dose of 50 mg per kg of body weight. Blood pressure readings were obtained at four hours (and in some cases also at 24 hours) after dosing. A compound was rated active if the post-treatment blood pressure was significantly depressed ($P \leq 0.05$) relative to the initial pressure reading.

Spontaneously Hypertensive Rat Assay—Direct Measurement

Male spontaneously hypertensive rats were used in this assay. Using a previously implanted arterial catheter, initial mean arterial blood pressure was measured directly immediately before administration of test compounds. For initial screening the test compounds were administered intragastrically at a dose of 50 mg per kg of body weight. Blood pressure readings were usually obtained at 1, 2, 3, and 4 hours after dosing. A compound was rated active if the mean post-treatment blood pressure was significantly different ($P \leq 0.05$) from that of the concurrent placebo control group.

Renal-ligated Hypertensive Rat Assay

Male Sprague Dawley rats aged 11 to 15 weeks old were used in this test. Three hours after bilateral ligation of the renal arteries, the mean arterial blood pressure (measured directly with previously implanted arterial catheters) and the plasma renin activity increased significantly ($P \leq 0.05$) higher than in sham-operated animals. Test compounds were administered intraarterially at a dose of 10 mg per kg of body weight, and blood pressure changes were monitored directly at 5, 10, and 15 minutes after injection. A compound was considered active if the post-treatment blood pressure was significantly ($P \leq 0.05$) depressed relative to the placebo control. Under these test conditions pepstatin significantly reduced both mean arterial blood pressure and plasma renin activity.

Rhesus Monkey Blood Pressure Test

Rhesus monkeys were sodium depleted by means of a fruit diet in combination with intramuscular furosemide injections (0.5 mg per kg of body weight) given twice daily for four days. This procedure causes blood pressure to become dependent on plasma renin activity. J. Burton, R. J. Cody, Jr., A. J. Herd, and E. Haber, *Proc. Natl. Acad. Sci. U. S. A.*, 77, 5476–5479 (1980). On the fifth day the animals were anesthetized with ketamine (100 mg administered intravenously). The femoral artery was cannulated for blood pressure measurement and a percutaneous venous cannula was inserted for test compound administration. The animals were allowed to recover from anesthesia and were restrained in a transparent plastic chair. Blood pressure was monitored continuously both before and after test compounds were administered (at 3 mg per kg of body weight). A compound was considered active if post-treatment mean blood pressure was significantly ($P \leq 0.05$) depressed relative to preadministration mean blood pressure. Under these test conditions captopril at 0.1 mg per kg and "renin inhibitory peptide" (RIP, or prolylhistidylprolylphenylalanylhistidylphenylalanyl-phenylalanylvalyltyrosyllysine; see Burton et al., supra) at 1.0 mg per kg significantly lowered mean blood pressure. By virtue of their renin inhibition activity, the compounds of Formula I are useful in treating or preventing symptoms of hypertension in humans and animals. A physician of ordinary skill could readily determine a subject who is exhibiting such symptoms. Regardless of the route of administration selected, the compounds of the present invention are formulated into pharmaceutically acceptable dosage forms by conventional methods known to the pharmaceutical art. The compounds can be administered in such oral dosage forms as tablets, capsules, pills, powders, granules, suspensions, or solutions. They may also introduced in the form of eyedrops, intraperitoneally, subcutaneously or intramuscularly, using forms known to the pharmaceutical art. In general the preferred form of administration is oral.

An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration of the particular compound employed. An ordinary skilled physician will readily determine and prescribe the effective amount based on the route of administration of the antihypertensive agent to prevent or arrest the progress of the condition. In so proceeding, the physician could employ relatively low dosages at first, subsequently increasing the dose until a maximum response is obtained. Suitable dosages for administration in the treatment or prevention of hypertension will ordinarily range between about 1.0 to 50 mg/kg up to a maximum of about 200 mg/kg.

The compounds of Formula I can also be administered as pharmacologically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention may be prepared by any number of methods known to those skilled in the art. For example, the particular sequence of reactions by which the individual amino acids are joined to form the compounds of Formula I is generally not of critical importance, being chosen principally for convenience or for maximum yields. Moreover, the choice of activating reagents and conditions for joining amino acids or small peptides is not limited to those specifically described herein. Peptide intermediates and products of this invention are typically purified by crystallization, where possible, or by column chromatography. Furthermore, where racemic amino acid starting materials are employed, intermediates and products may be separated during column chromatography into diastereomers. For example, reaction of racemic-t-butoxycarbonyl-2,6-dimethyl(D,L) tyrosine with a peptide intermediate results in racemic mixtures of diastereomeric products. Based upon thin layer chromatography results, these diastereomers are comprised of a slow moving isomer (S) and a faster moving isomer (F). In describing these isomers herein, the assumption is made that the slow moving diastereomer (S) corresponds to the L-isomer and the fast moving diasteriomer (F) corresponds to the D-isomer form of the tyrosyl starting material.

The accompanying Charts are used to illustrate one of the possible methods used to prepare the compounds of this invention.

Chart A illustrates a general method for forming dipeptide intermediates useful in the synthesis of compounds of Formula I. Partially blocked amino acids of Formula XI, in which B represents common N-protecting groups such as t-butoxycarbonyl, may be activated by any of several methods known to those skilled in the art. The generally preferred method includes forming a mixed anhydride by reaction with an alkyl chlorocarbonate in an unreactive solvent containing a tertiary amine. Preferred conditions include cooling a mixture of the appropriate compound of Formula XI in cold (ca. $-30°$ to $-40°$) dimethylformamide or dichloromethane containing N-methylmorpholine, followed by addition of isobutyl chloroformate. Once the mixed anhydride of Formula XII ($X = OCOOCH_2CH(CH_3)_2$) has formed, the appropriate amine of Formula XIII is added and the reaction allowed to proceed at room temperature, giving the fully blocked intermediates of Formula XIV.

Especially where the amine of Formula XIII is N-substituted (i.e., where $R_5$ is not hydrogen), an alternative method of activation involving carbodiimides may be more appropriate. For this method, compounds of Formulas XI and XIII are stirred together in an unreactive solvent to which is then added the carbodiimide. Preferred conditions include reaction in dichloromethane using dicyclohexylcarbodiimide. The isolated intermediates, Formula XIV, are exactly the same as those formed by the mixed anhydride method.

Using methods appropriate for the particular protecting groups B, compounds of Formula XIV may readily be deprotected to give compounds XV. Where the t-butoxycarbonyl protecting group is employed, for example, preferred deblocking conditions include acid solvolysis in hydrogen chloride/dioxane. Typically, the resultant hydrochloride salts may be used in subsequent reactions without first isolating the free amine.

Chart B illustates one method for extending the peptide chain to form intermediates of Formula XXVII. Using methods described above (see also Chart A), fully N-deprotected intermediates of Formula XXIV are formed from N-protected amino acids, Formula XXI, and omega-amino esters, Formula XXIII. Hydrolysis of these intermediates, Formula XXIV, affords the analogous acids of Formula XXV. Preferred hydrolysis conditions include approximately molar sodium hydroxide in aqueous methanol, followed by neutralization with sodium bisulfate. Using the methods described above, compounds of Formula XXV are activated and then coupled with intermediates of Formula XV to form N-(or)deprotected peptides of Formula XXVI. As described above (see Chart A), removal of the protecting groups B affords amino compounds of Formula XXVII.

Chart C illustrates one method for completing the extension of the peptide chains. As described before (see Charts A and B), suitably protected aromatic amino acids of Formula XXXI are activated, for example by using mixed anhydride or carbodiimide methods, and allowed to react with intermediates of Formula XXVII. Appropriate removal of protecting groups from compounds XXXII affords compounds of this invention, Formula I.

Chart D illustrates one method for preparing sulfoxide or sulfone members of this invention, Formula XLII (i.e., Formula I where $R = CH_2CH_2S(O)CH_3$ or $R = CH_2CH_2SO_2-CH_3$, respectively), which for practical reasons are generally prepared after the methionine-containing peptides of Formula XLI have been fully formed using methods described above. Preferred oxidizing conditions include hydrogen peroxide in aqueous methanol—at room temperature, sulfoxides are the predominant or sole oxidation product, whereas at elevated temperatures (e.g., refluxing solvent), sulfones are formed.

The invention will appear more fully from the examples which follow. These examples are given by way of illustration only, and are not to be construed as limiting the invention either in spirit or in scope, as many modifications both in materials and in methods will be apparent from this disclosure to those skilled in the art.

DESCRIPTION OF THE PREFERRED EMBODIMENTS

Example 1 t-butoxycarbonyl-N-(5-methoxy-5-oxopentyl)-L-phenylalaninamide

To a cold (ca $-30°$), stirred solution of 26.5 g (0.1 mole) of t-butoxycarbonylphenylalanine (BOC-Phe) and 11.2 g (0.1 mole) of N-methylmorpholine in 150 ml of dimethylformamide (DMF) was added dropwise 13.2 ml (0.1 mole) of isobutylchloroformate. After warming and then holding the temperature at ca. $-15°$ for about ten minutes, the solution was recooled to ca. $-39°$. To the cold mixture was added additional N-methylmorpholine (12.3 ml, ca. 0.11 mole), followed by 18.5 g (0.11 mole) of methyl 5-aminopentanoate hydrochloride. The mixture was allowed to warm to room temperature and to stand overnight. Solvent and other volatiles were removed by concentration in vacuo. The residue was triturated with ethyl acetate, which was then washed successively with water, 0.5M potassium bisulfate, water, and again with 0.5M potassium bisulfate, and then dried over magnesium sulfate, filtered, and concentrated to a white solid. After collection, the white solid was washed thoroughly with Skellysolve B to give 36.4 g of the title compound, m.p. 98°–100°. Recrystallization from ethyl acetate/Skellysolve B afforded analytically pure crystals.

Analysis. Calcd. For $C_{20}H_{30}N_2O_5$: C, 63.47; H, 7.99; N, 7.40. Found: C, 63.32; H, 8.03; N, 7.24.

Example 2 t-butoxycarbonyl-N-(6-methoxy-6-oxohexyl)-L-phenylalaninamide

The title compound was prepared by the method of Example 1 using methyl 6-aminohexanoate hydrochloride and was used in subsequent reactions without further purification.

Example 3

N-(6-methoxy-6-oxohexyl)-L-phenylalaninamide monohydrochloride

To a solution of the title compound of Example 2 (43.1 g, 0.11 mole) in 100 ml of dioxane was added 100 ml of 6M hydrogen chloride/dioxane. After about 30 min. the solution was concentrated in vacuo to dryness and the residue triturated thoroughly with diethyl ether. The solid was collected and washed well with diethyl ether, giving 34.7 g of the title compound, which was used in subsequent reactions without further purification.

Example 4

N-(4-methoxy-4-oxobutyl)-L-phenylalaninamide monohydrochloride

The title compound was prepared by the methods of Examples 1 and 3 using methyl 4-aminobutanoate hydrochloride and was used in subsequent reactions without further purification.

Example 5

N-(5-methoxy-5-oxopentyl)-L-phenylalaninamide monohydrochloride

The title compound was prepared by the method of Example 3 using the title compound of Example 1 and was used in subsequent reactions without further purification.

Example 6

N-(7-methoxy-7-oxoheptyl)-L-phenylalaninamide monohydrochloride

The title compound was prepared by the methods of Examples 1 and 3 using methyl 7-aminoheptanoate hydrochloride and was used in subsequent reactions without further purification.

Example 7

N-(8-methoxy-8-oxooctyl)-L-phenylalaninamide monohydrochloride

The title compound was prepared by the methods of Examples 1 and 3 using methyl 8-aminooctanoate hydrochloride and was used in subsequent reactions without further purification.

Example 8 t-butoxycarbonyl-D-methionylglycine methyl ester

The title compound was prepared by the general method of Example 1 using 24.9 g (0.1 mole) of t-butoxycarbonyl-D-methionine (BOC-D-Met) and 13.8 g (0.11 mole) of glycine methyl ester hydrochloride. The crude product was recrystallized from ethyl acetate/Skellysolve B to give the title compound, which was used in subsequent reactions without further purification.

Example 9 t-butoxycarbonyl-D-methionylglycine

The title compound of Example 8 (32.0 g, 0.1 mole) was dissolved in 200 ml of methanol to which was added 200 ml of 2M potassium hydroxide. After ca. 5 min. at room temperature the solution was concentrated to about half volume and diluted with ethyl acetate. The solution was neutralized by washing with two portions of 0.5M potassium bisulfate, and then dried over magnesium sulfate, filtered, and concentrated in vacuo. The crude product was recrystallized to give the title compound, which was used in subsequent reactions without further purification.

Example 10 t-butoxycarbonyl-D-methionylglycyl-N-(6-methoxy-6-oxohexyl)-L-phenylalaninamide

A mixture of the title compounds of Example 3 (28.9 g, 0.088 mole) and Example 9 (27.2 g, 0.084 mole) in 150 ml of dichloromethane was solubilized by warming and adding 9.8 ml (ca. 0.087 mole) of N-methylmorpholine. After the solution was cooled to ca. 0°, 18.2 g (0.088 mole) of dicyclohexylcarbodiimide in 50 ml of dichloromethane was added, and the reaction mixture was allowed to warm to room temperature. After a total of four hours, insolubles were removed by filtration and the filtrate was washed sequentially with two portions of 0.5M potassium bisulfate. The organic phase was dried over magnesium sulfate, filtered, and concentrated in vacuo. The crude material was purified by column chromatography on silica gel to give the title compound (42.0 g).

Analysis. Calcd. for $C_{28}H_{44}N_4O_7S$: C, 57.91; H, 7.64; N, 9.65; S, 5.52. Found: C, 57.84; H, 7.75; N, 9.89; S, 5.55.

Example 11

D-methionylglycyl-N-(6-methoxy-6-oxohexyl)-L-phenylalaninamide monohydrochloride hemihydrate The title compound of Example 10 (12.0 g) was dissolved in 50 ml of dioxane to which was added 50 ml of 6M hydrogen chloride/dioxane. After about one hour, the volatiles were removed in vacuo and the residue triturated thoroughly with diethyl ether. The title compound (10.9 g) was collected as an analytically pure hydrochloride hemihydrate.

Analysis. Calcd. for $C_{23}H_{36}N_4O_5S \cdot HCl \cdot \frac{1}{2}H_2O$: C, 52.51; H, 7.28; N, 10.65; S, 6.09; Cl, 6.74. Found: C, 52.33; H, 7.24; N, 10.68; S, 6.14; Cl, 6.69.

Example 12 t-butoxycarbonyl-2,6-dimethyltyrosine

To a stirred solution of 100 g (820 mmole) of 3,5-dimethylphenol and 79 g (1 mole) of pyridine in 300 ml of cooled (5°–10°) toluene was slowly added 109 g (1 mole) of ethyl chloroformate in 100 ml of toluene. After overnight stirring, the mixture was concentrated in vacuo to an oil which was purified by distillation at reduced pressure, giving an intermediate carbonate diester. After heating 250 ml of concentrated hydrochloric acid to ca. 55°, 22 g of 37% aqueous formaldehyde was added, followed by addition of the carbonate diester. Hydrogen chloride gas was bubbled through the solution for about six hours. The mixture was allowed to stand overnight at room temperature and then shaken with dichloromethane. The organic phase thus formed was washed with water, aqueous sodium bicarbonate, and saturated brine, and then dried over sodium sulfate, filtered, and concentrated in vacuo. The resultant 4-chloromethyl derivative was purified by distillation at reduced pressure. After preparing an ethanolic solution of sodium ethoxide from 2.5 g (110 mmole) of sodium metal, 21.7 g (100 mmole) of diethyl acetamidomalonate was added and the solution heated to reflux. An ethanolic solution of the 4-chloromethyl intermediate was then added and the mixture was heated at reflux for another 2.5 hours. After standing overnight at room temperature, the mixture was treated with 6.6 g (110 mmole) of acetic acid. The resultant gum was dissolved in dichloromethane, which was then washed with aqueous sodium bicarbonate, filtered, and concentrated in vacuo to an oily residue. Recrystallization from diethyl ether afforded 6.5 g of the benzyl malonate derivative (from which the O-ethyoxycarbonyl group was lost). Heating a 1.0 g portion of the malonate derivative in concentrated hydrochloric acid at 95° for about three days afforded 680 mg of 2,6-dimethyltyrosine as the nearly analytically pure hydrated hydrochloride salt. [Analysis. Calcd. for $C_{11}H_{15}NO_3 \cdot HCl \cdot H_2O$: C, 50.09; H, 6.13; N, 5.31; Cl, 13.44. Found: C, 49.36; H, 6.30; N, 5.20; Cl, 14.10.] About 45 g of the amino acid prepared as above was then dissolved in ca. 400 ml of ice water, which was adjusted to about pH 10. Di-t-butyl dicarbonate (41 g) was added, with maintenance of pH to 13 to saponify O-butoxycarbonyl groups, the mixture was cooled to about 0° and adjusted to pH 2. The crude title compound was extracted into ethyl acetate, which was washed with saturated brine, dried over sodium sulfate, filtered, and dried under a stream of nitrogen. Recrystallization from ethyl acetate afforded analytically pure BOC-protected compound.

Analysis. Calcd. for $C_{16}H_{23}NO_5$: C, 62.12; H, 7.49; N, 4.53. Found: C, 61.87; H, 7.51; N, 4.34.

Example 13 t-butoxycarbonyl-2,6-dimethyl-(D and L)-tyrosyl-D-methionylglycyl-N-(6-methoxy-6-oxohexyl)-L-phenylalaninamide The title compound was prepared by the method of Example 1 using 6.80 g (0.022 mole) of t-butoxycarbonyl-2,6-dimethyltyrosine and the title compound of Example 11 (10.8 g, 0.020 mole). A portion of the crude racemic product (4.5 g) was purified by column chromatography on silica gel (methanol/chloroform eluent) to give 1.79 g of the D isomer and 2.11 g of the L isomer. The individual isomeric components, differing in the alpha-carbon stereochemistry of the 2,6-dimethyltyrosine moiety, were used without further purification in subsequent reactions.

Example 14

2,6-dimethyl-L-tyrosyl-D-methionylglycyl-N-(6-methoxy-6-oxohexyl)-L-phenylalaninamide monohydrochloride monohydrate (SC-36739)

The L isomer of the title compound of Example 13 (2.11 g) was dissolved in 20 ml of acetic acid to which was added 20 ml of 6M hydrogen chloride/dioxane. After one hour at room temperature, volatiles were removed in vacuo and the residue triturated thoroughly with diethyl ether. The title compound was collected as 1.95 g of an analytically pure solid.

$[\alpha]_D + 5.3°$; $[\alpha]_{365} + 187.8°$ (methanol)

Analysis. Calcd. for $C_{34}H_{49}N_5O_7S \cdot HCl \cdot H_2O$: C, 56.23; H, 7.22; N, 9.64; S, 4.41; Cl, 4.88. Found: C, 56.19; H, 7.04; N, 9.57; S, 4.33; Cl, 4.99.

Example 15

2,6-dimethyl-D-tyrosyl-D-methionylglycyl-N-(6-methoxy-6-oxohexyl)-L-phenylalaninamide monohydrochloride monohydrate (SC-36738)

The title compound was prepared by the method of Example 14 using the D isomer of Example 13.

Analysis. Calcd. for $C_{34}H_{49}N_5O_7S \cdot HCl \cdot H_2O$: C, 56.23; H, 7.22; N, 9.64; S, 4.41; Cl, 4.88. Found: C, 56.19; H, 7.04; N, 9.57; S, 4.33; Cl, 4.99. $[\alpha]_D - 51.1°$; $[\alpha]_{365}$

Example 16

2,6-dimethyl-L-tyrosyl-[4-(methylsulfinyl)-D-2-aminobutanoyl]glycyl-N-(6-methoxy-6-oxohexyl)-L-phenylalaninamide monohydrochloride 2½ hydrate (SC-36755)

To a solution of the title compound of Example 14 (0.71 g, 1.0 mmole) in 3.5 ml of water and 3.5 ml of methanol was added 0.5 ml of 10M hydrogen peroxide. After one hour at room temperature, the reaction was diluted with water to about 70 ml, filtered, and the filtrate lyophilized. The title compound (0.68 g) was isolated as an analytically pure hydrated solid.

$[\alpha]_D + 46.7°$; $[\alpha]_{365} + 172.0°$ (methanol)

Analysis. Calcd. for $C_{34}H_{49}N_5O_8S \cdot HCl \cdot 2\frac{1}{2}H_2O$: C, 53.08; H, 7.20; N, 9.10; S, 4.17; Cl, 4.61. Found: C, 52.78; H, 6.57; N, 8.95; S, 4.35; Cl, 4.70.

Example 17

2,6-dimethyl-D-tyrosyl-[4-(methylsulfinyl)-D-2-aminobutanoyl]glycyl-N-(6-methoxy-6-oxohexyl)-L-phenylalaninamide monohydrochloride 2½ hydrate (SC-36773)

The title compound was prepared by the method of Example 16 using the title compound of Example 15.

Analysis. Calcd. for $C_{34}H_{49}N_5O_8S \cdot HCl \cdot 2\frac{1}{2}H_2O$: C, 53.08; H, 7.20; N, 9.10; S, 4.17; Cl, 4.61. Found: C, 52.96; H, 6.71; N, 9.04; S, 4.24; Cl, 4.55.

Example 18

2,6-dimethyltyrosyl-[4-(methylsulfinyl)-D-2-aminobutanoyl]glycyl-N-(6-methoxy-6-oxohexyl)-L-phenylalaninamide monohydrochloride sesquihydrate (SC-34973)

The title compound was prepared from an unresolved mixture of the compound mixture of Example 13 using the methods of Examples 14 and 16.

Analysis. Calcd. for $C_{34}H_{49}N_5O_8S \cdot HCl \cdot 3/2H_2O$: C, 54.35; H, 7.11; N, 9.32; S, 4.27; Cl, 4.72. Found: C, 54.20; H, 6.80; N, 9.23; S, 4.17; Cl, 4.70.

Example 19

2,6-dimethyl-L-tyrosyl-D-methionylglycyl-N-(5-methoxy-5-oxopentyl)-L-phenylalaninamide monohydrochloride monohydrate (SC-36589)

The title compound was prepared by the methods of Examples 10, 11, 13, and 14 using the title compound of Example 5.

Analysis. Calcd. for $C_{33}H_{47}N_5O_7 \cdot HCl \cdot H_2O$: C, 55.65; H, 7.08; N, 9.83; S, 4.50; Cl, 4.98. Found: S, 56.00; H, 7.06; N, 9.61; S, 4.09; Cl, 5.01.

Example 20

2,6-dimethyl-D-tyrosyl-D-methionylglycyl-N-(5-methoxy-5-oxopentyl)-L-phenylalaninamide monohydrochloride monohydrate (SC-36588)

The title compound was prepared by the methods of Examples 10, 11, 13, and 15 using the title compound of Example 5.

Analysis. Calcd. for $C_{33}H_{47}N_5O_7S \cdot HCl \cdot H_2O$: C, 55.65; H, 7.08; N, 9.83; S, 4.50; Cl, 4.98. Found: C, 55.84; H, 7.03; N, 9.77; S, 4.43; Cl, 5.21.

Example 21

2,6-dimethyl-L-tyrosyl-[4-methylsulfinyl)-D-2-aminobutanoyl]glycyl-N-(5-methoxy-5-oxopentyl)-L-phenylalaninamide monohydrochloride 2½ hydrate (SC-36655)

The title compound was prepared by the method of Example 16 using the title compound of Example 19.

Analysis. Calcd. for $C_{33}H_{47}N_5O_8S \cdot HCl \cdot 2\frac{1}{2}H_2O$: C, 52.48; H, 4.07; N, 9.27; S, 4.25; Cl, 4.69. Found: C, 52.31; H, 6.58; N, 9.16; S, 4.30.

Example 22

2,6-dimethyl-D-tyrosyl-[4-methylsulfinyl)-D-2-aminobutanoyl]glycyl-N-(5-methoxy-5-oxopentyl)-L-phenylalaninamide monohydrochloride The title compound is prepared by the method of Example 16 using the title compound of Example 20.

Example 23

2,6-dimethyl-L-tyrosyl-D-methionylglycyl-N-(7-methoxy-7-oxoheptyl)-L-phenylalaninamide monohydrochloride monohydrate (SC-36777)

The title compound was prepared by the methods of Examples 10, 11, 13, and 14 using the title compound of Example 6.

Analysis. Calcd. for $C_{35}H_{51}N_5O_7S \cdot HCl \cdot H_2O$: C, 56.78; H, 7.35; N, 9.46; S, 4.33; Cl, 4.79. Found: C, 56.84; H, 7.07; N, 9.60.

Example 24

2,6-dimethyl-D-tyrosyl-D-methionylglycyl-N-(7-methoxy-7-oxoheptyl)-L-phenylalaninamide monohydrochloride hemihydrate (SC-36776)

The title compound was prepared by the methods of Examples 10, 11, 13, and 15 using the title compound of Example 6.

Analysis. Calcd. for $C_{35}H_{51}N_5O_7S \cdot HCl \cdot \frac{1}{2}H_2O$: C, 57.48; H, 7.30; N, 9.58; S, 4.38; Cl, 4.85. Found: C, 57.36; H, 7.11; N, 9.61.

Example 25

2,6-dimethyl-L-tyrosyl-[4-(methylsulfinyl)-D-2-aminobutanoyl]glycyl-N-(7-methoxy-7-oxoheptyl)-L-phenylalaninamide monohydrochloride (SC-36922)

The title compound was prepared by the method of Example 16 using the title compound of Example 23.

Analysis. Calcd. for $C_{35}H_{51}N_5O_8S \cdot HCl$: C, 54.93; H, 7.24; N, 9.15; S, 4.19. Found: C, 54.96; H, 6.96; N, 9.17; S, 4.19.

Example 26

2,6-dimethyl-D-tyrosyl-[4-(methylsulfinyl)-D-2-aminobutanoyl]glycyl-N-(7-methoxy-7-oxoheptyl)-L-phenylalaninamide monohydrochloride sesquihydrate (SC-36921)

The title compound was prepared by the method of Example 16 using the title compound of Example 24.

Analysis. Calcd. for $C_{35}H_{51}N_5O_8S \cdot HCl \cdot 3/2H_2O$: C, 54.93; H, 7.24; N, 9.15; S, 4.19; Cl, 4.63. Found: C, 54.57; H, 6.92; N, 9.08; S, 3.83.

Example 27

2,6-dimethyl-L-tyrosyl-D-methionylglycyl-N-(8-methoxy-8-oxooctyl)-L-phenylalaninamide monohydrochloride hemihydrate (SC-36338)

The title compound was prepared by the method of Examples 10, 11, 13, and 14 using the title compound of Example 7.

Analysis. Calcd. for $C_{36}H_{53}N_5O_7S \cdot HCl \cdot \frac{1}{2}H_2O$: C, 58.01; H, 7.44; N, 9.40; S, 5.41. Found: C, 57.85; H, 7.68; N, 9.40; S, 5.22.

Example 28

2,6-dimethyl-D-tyrosyl-D-methionylglycyl-N-(8-methoxy-8-oxooctyl)-L-phenylalaninamide monohydrochloride monohydrate (SC-36337)

The title compound was prepared by the methods of Examples 10, 11, 13, and 15 using the title compound of Example 7.

Analysis Calcd. for $C_{36}H_{53}N_5O_7S \cdot HCl \cdot H_2O$: C, 57,32; H, 7.48; N, 9.28; Cl, 4.70. Found: C, 57.33; H, 7.51; N, 9.13; Cl, 5.41.

Example 29

2,6-dimethyl-L-tyrosyl-[4-(methylsulfinyl)-D-2-aminobutanoyl]glycyl-N-(8-methoxy-8-oxooctyl)-L-phenylalaninamide monohydrochloride monohydrate (SC-36344)

The title compound was prepared by the methods of Example 15 using the title compound of Example 27.

Analysis. Calcd. for $C_{36}H_{53}N_5O_8S \cdot HCl \cdot H_2O$: C, 56.13; H, 7.33; N, 9.09; Cl, 4.60. Found: C, 56.04; H, 7.22; N, 9.06, Cl, 4.81.

Example 30

2,6-dimethyl-D-tyrosyl-[4-(methylsulfinyl)-D-2-aminobutanoyl]glycyl-N-(8-methoxy-8-oxooctyl)-L-phenylalaninamide monohydrochloride monohydrate (SC-36392)

The title compound was prepared by the method of Example 16 using the title compound of Example 28.

Analysis. Calcd. for $C_{36}H_{53}N_5O_8S \cdot HCl \cdot H_2O$: C, 56.13; H, 7.33; N, 9.09. Found: C, 55.76; H, 7.18; N, 9.02.

Example 31

2,6-dimethyltyrosyl-[4-(methylsufinyl)-D-2-aminobutanoyl]glycyl-N-(4-methoxy-4-oxobutyl)-L-phenylalaninamide monohydrochloride sesquihydrate (SC-34972)

The title compound was prepared by the methods of Examples 10, 11, 13 (except that the racemic mixture was not resolved), 14, and 16 using the title compound of Example 4.

Analysis. Calcd. for $C_{32}H_{45}N_5O_8S \cdot HCl \cdot 3/2H_2O$: C, 53.14; H, 6.83; N, 9.68; S, 4.43; Cl, 4.90. Found: C, 53.27; H, 6.55; N, 9.34; S, 4.42; Cl, 5.37.

Example 32

L-tyrosyl-D-methionylgycyl-N-(6-methoxy-6-oxohexyl)-L-phenylalaninamide monohydrochloride sesquihydrate (SC-36798)

The title compound was prepared using the methods of Examples 13 and 14 using t-butoxycarbonyltyrosine in place of t-butoxycarbonyl-2,6-dimethyltyrosine. Structure assignment was supported by elemental analysis.

Analysis. Calcd. for $C_{32}H_{45}N_5O_7S \cdot HCl \cdot 3/2H_2O$: C, 54.34; H, 6.98; N, 9.90; S, 4.53; Cl, 5.01. Found: C, 54.30; H, 6.61; N, 9.82; S, 4.19; Cl, 5.61.

Example 33

L-tyrosyl-[4-(methylsulfinyl)-D-2-aminobutanoyl]glycyl-N-(6-methoxy-6-oxohexyl)-L-phenylalaninamide monohydrochloride monohydrate (SC-36801)

The title compound was prepared by the method of Example 16 using the title product of Example 32. Structure assignment was supported by elemental analysis.

Analysis. Calcd. for $C_{32}H_{45}N_5O_8S \cdot HCl \cdot H_2O$: C, 53.81; H, 6.77; N, 9.81; S, 4.49; Cl, 5.21. Found: C, 53.46; H, 6.55; N, 9.80; S, 4.23; Cl, 5.21.

Example 34

$N^\alpha$-methyl-L-tyrosyl-D-methionylglycyl-N-(6-methoxy-6-oxohexyl)-L-phenylalaninamide monohydrochloride hemihydrate (SC-36814)

The title compound was prepared using the methods of Examples 13 and 14 using t-butoxycarbonyl-N-methyltyrosine in place of t-butoxycarbonyl-2,6-dimethyltyrosine. Structure assignment was supported by elemental analysis.

Analysis. Calcd. for $C_{33}H_{47}N_5O_7S \cdot HCl \cdot H_2O$: C, 56.36; H, 7.02; N, 9.96; S, 4.07; Cl, 5.04. Found: C, 56.21; H, 6.90; N, 9.81; S, 4.47; Cl, 5.14.

Example 35

$N\alpha$-methyl-L-tyrosyl-[4-(methylsulfinyl)-D-2-aminobutanoyl]glycyl-N-(6-methoxy-6-oxohexyl)-L-phenylalaninamide monohydrochloride 1¼ hydrate (SC-36816)

The title compound was prepared by the method of Example 16 using the title product of Example 34. Structure assignment was supported by elemental analysis.

Analysis. Calcd. for $C_{33}H_{47}N_5O_8S \cdot HCl \cdot \frac{1}{4}H_2O$: C, 54.09; H, 6.95; N, 9.56; S, 4.37; Cl, 4.84. Found: C, 53.96; H, 6.69; N, 9.53; S, 4.26; Cl, 4.95.

Example 36 t-butoxycarbonyl-2,4,6-trimethylphenylalanine

After preparing an ethanolic solution of sodium ethoxide from 30.1 g (1.31 mole) of sodium metal, 200 g (1.19 mole) of diethyl acetamidomalonate was added and the solution heated to reflux. An ethanolic solution of the 2,4,6-trimethylbenzyl chloride was then added and the mixture was heated at reflux for another four hours. The mixture was concentrated in vacuo and the residue triturated multiply with water, then with dichloromethane. After removing insolubles by filtration, the filtrate was washed with brine, decolorized with activated carbon, filtered, concentrated to a small volume, and allowed to stand. Repetition of the decolorization, followed by recrystallization from Skellysolve B afforded the analytically pure benzyl malonate derivative. A portion of the malonate (12 g, 36 mmole) was heated at reflux in a mixture of 50 ml ethanol and 50 ml concentrated hydrochloric acid for about four days. Upon cooling, racemic 2,4,6-trimethylphenylalanine precipitated. The BOC-protected title compound was prepared using di-t-butyl dicarbonate as described in Example 12.

Example 37

2,6-dimethyl-L-tyrosyl-D-methionylglycyl-N-(6-methoxy-6-oxohexyl)-2,4,6-trimethylphenylalaninamide monohydrochloride monohydrate (SC-39724)

After preparing N-(6-methoxy-6-oxohexyl)-2,4,6-trimethylphenylalaninamide monohydrochloride from the title product of Example 36 by the methods of Examples 1 and 3, the title compound was prepared by the methods described in Examples 10, 11, 13, and 14. Structure assignment was supported by elemental analysis.

Analysis. Calcd. for $C_{37}H_{55}N_5O_7S \cdot HCl \cdot H_2O$: C, 57.84; H, 7.61; N, 9.11; S, 4.17; Cl, 4.61. Found: C, 58.12; H, 7.55; N, 8.96; S, 4.13; Cl, 5.07.

Example 38

2,6-dimethyl-D-tyrosyl-D-methionylglycyl-N-(6-methoxy-6-oxohexyl)-2,4,6-trimethylphenylalaninamide monohydrochloride hemihydrate (SC-39699)

The title compound was prepared by the methods summarized in Example 37, except for using the method of Example 15 instead of Example 14. Structure assignment was supported by elemental analysis.

Analysis. Calcd. for $C_{37}H_{55}N_5O_7S \cdot HCl \cdot \frac{1}{2}H_2O$: C, 58.52; H, 7.57; N, 9.22; S, 4.22; Cl, 4.67. Found: C, 58.44; H, 7.58; N, 8.88; S, 4.19; Cl, 4.94.

Example 39

2,6-dimethyl-L-tyrosyl-[4-(methylsulfinyl)-D-2-aminobutanoyl]glycyl-N-(6-methoxy-6-oxohexyl)-2,4,6-trimethylphenylalaninamide monohydrochloride sesquihydrate (SC-40178)

The title compound was prepared by the method of Example 16 using the title product of Example 37. Structure assignment was supported by elemental analysis.

Analysis. Calcd. for $C_{37}H_{55}N_5O_8S \cdot HCl \cdot 3/2H_2O$: C, 56.01; H, 7.50; N, 8.83; S, 4.04; Cl, 4.47. Found: C, 55.84; H, 7.20; N, 8.80; S, 4.01; Cl, 4.56.

Example 40

2,6-dimethyl-D-tyrosyl-[4-(methylsulfinyl)-D-2-aminobutanoyl]glycyl-N-(6-methoxy-6-oxohexyl)-2,4,6-trimethylphenylalaninamide monohydrochloride sesquihydrate (SC-40075)

The title compound was prepared by the method of Example 16 using the title product of Example 38. Structure assignment was supported by elemental analysis.

Analysis. Calcd. for $C_{37}H_{55}N_5O_8S \cdot HCl \cdot 3/2H_2O$: C, 56.01; H, 7.50; N, 8.83; S, 4.04; Cl, 4.47. Found: C, 56.23; H, 7.32; N, 8.78; S, 4.16; Cl, 4.60.

Example 41

2,6-dimethyl-L-tyrosyl-D-methionylglycyl-N-(6-hydroxyhexyl)-L-phenylalaninamide monohydrochloride monohydrate (SC-39782)

Using 6-aminohexanol instead of an omega-aminoalkanoic acid, t-butoxycarbonyl-N-(6-hydroxyhexyl)-L-phenylalaninamide was prepared by the general method of Example 1. Using the method of Example 3, except for adding about an equal volume of acetic acid to facilitate solution, the N-protected precursor was converted to N-(6-acetyloxyhexyl)-L-phenylalaninamide. After then proceeding by the methods of Examples 10, 11, and 13, the intermediate terminal O-acetyl group was removed by the method of Example 9. Finally, the title compound was prepared using the method of Example 11. Structure assignment was supported by elemental analysis.

Analysis. Calcd. for $C_{33}H_{49}N_5O_6S \cdot HCl \cdot H_2O$: C, 56.76; H, 7.50; N, 10.03; S, 4.59; Cl, 5.08. Found: C, 56.57; H, 7.50; N, 9.74; S, 4.45; Cl, 5.39.

Example 42

2,6-dimethyl-D-tyrosyl-D-methionylglycyl-N-(6-hydroxyhexyl)-L-phenylalaninamide monohydrochloride monohydrate (SC-39781)

The title compound was prepared by the methods summarized in Example 41, except for using the method of Example 15 instead of Example 11 in the final step. Structure assignment was supported by elemental analysis.

Analysis. Calcd. for $C_{33}H_{49}N_5O_6S \cdot HCl \cdot H_2O$: C, 56.76; H, 7.50; N, 10.03; S, 4.59; Cl, 5.08. Found: C, 56.40; H, 7.48; N, 9.75; S, 4.41; Cl, 5.53.

Example 43

2,6-dimethyl-L-tyrosyl-[4-(methylsulfinyl)-D-2-aminobutanoyl]glycyl-N-(6-hydroxyhexyl)-L-phenylalaninamide monohydrochloride sesquihydrate (SC-40238)

The title compound was prepared by the method of Example 16 using the title product of Example 41. Structure assignment was supported by elemental analysis.

Analysis. Calcd. for $C_{33}H_{49}N_5O_7S \cdot HCl \cdot 3/2H_2O$: C, 54.87; H, 7.26; N, 9.70; S, 4.44; Cl, 4.91. Found: C, 54.57; H, 6.76; N, 9.41; S, 4.30; Cl, 5.12.

Example 44

2,6-dimethyl-D-tyrosyl-[4-(methylsulfinyl)-D-2-aminobutanoyl]glycyl-N-(6-hydroxyhexyl)-L-phenylalaninamide monohydrochloride dihydrate (SC-40192)

The title compound was prepared by the method of Example 16 using the title product of Example 42. Structure assignment was supported by elemental analysis.

Analysis. Calcd. for $C_{33}H_{49}N_5O_7S \cdot HCl \cdot 2H_2O$: C, 54.12; H, 7.43; N, 9.56; S, 4.38; Cl, 4.84. Found: C, 54.32; H, 6.79; N, 9.47; S, 4.31; Cl, 5.17.

Example 45

2,6-dimethyl-L-tyrosyl-D-methionylglycyl-N-(6-acetyloxyhexyl)-$N^\alpha$-methyl-L-phenylalaninamide monohydrochloride hemihydrate (SC-39745)

The title compound was prepared by the methods summarized in Example 41, except that t-butoxycarbonyl-N-methyl-L-phenylalanine was used instead of t-butoxycarbonylphenylalanine and the O-acetyl group was not removed before proceeding to the final reaction, which employed the method of Example 14. Structure assignment was supported by elemental analysis.

Analysis. Calcd. for $C_{36}H_{53}N_5O_7S \cdot HCl \cdot \frac{1}{2}H_2O$: C, 58.01; H, 7.30; N, 9.40; S, 4.30; Cl, 4.76. Found: C, 57.67; H, 7.21; N, 9.33; S, 4.46; Cl, 5.10.

Example 46

2,6-dimethyl-D-tyrosyl-D-methionylglycyl-N-(6-acetyloxyhexyl)-$N^\alpha$-methyl-L-phenylalaninamide monohydrochloride monohydrate (SC-39734)

The title compound was prepared by the methods of Example 45, except for using the method of Example 15 instead of Example 14 in the final step. Structure assignment was supported by elemental analysis.

Analysis. Calcd. for $C_{36}H_{53}N_5O_7S \cdot HCl \cdot H_2O$: C, 57.32; H, 7.48; N, 9.28; S, 4.25; Cl, 4.70. Found: C, 57.26; H, 7.24; N, 9.20; S, 4.30; Cl, 5.17.

Example 47

2,6-dimethyl-L-tyrosyl-D-methionylglycyl-N-(6-hydroxyhexyl)-$N^\alpha$-methyl-L-phenylalaninamide hydrochloride monohydrate (SC-40061)

The title compound was prepared (as the 1.2 HCl monohydrate) from the title product of Example 45 using the method of Example 9. Structure assignment was supported by elemental analysis.

Analysis. Calcd. for $C_{34}H_{51}N_5O_6S \cdot 1.2HCl \cdot H_2O$: C, 56.75; H, 7.59; N, 9.73; S, 4.46; Cl, 5.91. Found: C, 56.83; H, 7.38; N, 9.40; S, 4.36; Cl, 5.74.

Example 48

2,6-dimethyl-D-tyrosyl-D-methionylglycyl-N-(6-hydroxyhexyl)-$N^\alpha$-methyl-L-phenylalaninamide hydrochloride monohydrate (SC-40060)

The title compound was prepared (as the 1.2 HCl monohydrate) from the title product of Example 45 using the method of Example 9. Structure assignment was supported by elemental analysis.

Analysis. Calcd. for $C_{34}H_{51}N_5O_6S \cdot 1.2HCl \cdot H_2O$: C, 56.75; H, 7.59; N, 9.73; S, 4.46; Cl, 5.91. Found: 56.77; H, 7.37; N, 9.49; S, 4.45; Cl, 5.74.

Example 49

2,6-dimethyl-L-tyrosyl-[4-(methylsulfinyl)-D-2-aminobutanoyl]glycyl-N-(6-hydroxyhexyl)-N$^\alpha$-methyl-L-phenylalaninamide monohydrochloride sesquihydrate (SC-40446)

The title compound was prepared by the method of Example 16 using the title product of Example 47. Structure assignment was supported by elemental analysis.

Analysis. Calcd. for $C_{34}H_{51}N_5O_7S \cdot HCl \cdot 3/2H_2O$: C, 55.38; H, 7.52; N, 9.50; S, 4.35; Cl, 4.81. Found: C, 55.38; H, 7.23; N, 9.16; S, 4.26; Cl, 5.14.

Example 50

2,6-dimethyl-D-tyrosyl-[4-(methylsulfinyl)-D-2-aminobutanoyl]glycyl-N-(6-hydroxyhexyl)-N$^\alpha$-methyl-L-phenylalaninamide monohydrochloride dihydrate (SC-40358)

The title compound was prepared by the method of Example 16 using the title product of Example 48. Structure assignment was supported by elemental analysis.

Analysis. Calcd. for $C_{34}H_{51}N_5O_7S \cdot HCl \cdot 2H_2O$: C, 54.72; H, 7.56; N, 9.38; S, 4.30; Cl, 4.75. Found: C, 54.86; H, 7.48; N, 9.46; S, 4.29; Cl, 5.00.

Example 51 t-butoxycarbonyl-N-ethyl-L-tyrosine

To a stirred mixture of 18.6 g (50 mmole) of t-butoxycarbonyl-O-benzyl-L-tyrosine in 400 ml of freshly dried tetrahydrofuran cooled to −78° was added dropwise 58 ml of 1.9M t-butyl lithium in pentane. After warming to −20°, the solution was stirred for 1.5 hours, and 9.5 g (50 mmole) of triethyloxonium fluoborate was then added. After about one hour the mixture was poured into and shaken with aqueous sodium bisulfate (giving a pH of 3 in the aqueous phase). The aqueous phase was washed with water, dried over sodium sulfate, filtered, and concentrated in vacuo to an oil. Purification by column chromatography on silica gel afforded 12.6 g of the O-benzyl ether derivative of the title compound as a white solid. [Analysis. Calcd. for $C_{23}H_{29}NO_5$: C, 69.15; H, 7.32; N, 3.51. Found: C, 68.70; H, 7.22; N, 3.53.] A portion (1.0 g, 2.25 mmole) of the benzyl ether intermediate in 35 ml of tetrahydrofuran was hydrogenated at room temperature using hydrogen gas at atmospheric pressure and 5% palladium on carbon as catalyst. After filtration the filtrate was concentrated to dryness and purified by column chromatography, giving the analytically pure title compound.

$[\alpha]_D$ −124.4°; $[\alpha]_{365}$ −447.8° (chloroform)

Analysis. Calcd. for $C_{16}H_{23}NO_5$: C, 62.12; H, 7.49; N, 4.53. Found: C, 62.14; H, 7.81; N, 4.73.

EXAMPLE 52 t-butoxycarbonyl-N$^\alpha$-ethyl-O-(2-methylpropoxycarbonyl)-L-tyrosyl-D-methionylglycyl-N-(6-methoxy-6-oxohexyl)-L-phenylalaninamide

The title compound was prepared from 2.09 g (6.8 mmole) of the title product of Example 51 using the general method described in Example 13 (and Example 1) except that a two-fold quantity (1.77 ml, ca. 13.5 mmole) of isobutylchloroformate was employed. Purification by column chromatography on silica gel afforded 3.75 g of the title compound as an analytically pure glassy solid.

Analysis. Calcd. for $C_{44}H_{65}N_5O_{11}S$: C, 60.60; H, 7.51; N, 8.03; S, 3.68. Found: C, 60.55; H, 7.55; N, 8.02; S, 3.68.

Example 53

N$^\alpha$-ethyl-O-(2-methylpropoxycarbonyl)-L-tyrosyl-D-methionylglycyl-N-(6-methoxy-6-oxohexyl)-L-phenylalaninamide monohydrochloride (SC-36763)

The title compound was prepared by the method of Example 14 using 1.7 g (1.9 mmole) of the title product of Example 52. Structure assignment was supported by elemental analysis.

$[\alpha]_D$ +36.0; $[\alpha]_{365}$ +132.0 (methanol)

Analysis. Calcd. for $C_{39}H_{57}N_5O_9S \cdot HCl$: C, 57.94; H, 7.23; N, 8.66; S, 3.97; Cl, 4.38. Found: C, 57.79; H, 7.13; N, 8.77; S, 4.06; Cl, 4.46.

Example 54

N$^\alpha$-ethyl-O-(2-methylpropoxycarbonyl)-L-tyrosyl-[4-(methylsulfinyl)-D-2-aminobutanoyl]glycyl-N-(6-methoxy-6-oxohexyl)-L-phenylalaninamide monohydrochloride (SC-36792)

The title compound was prepared by the method of Example 16 using the title product of Example 53. Structure assignment was supported by elemental analysis.

Analysis. Calcd. for $C_{39}H_{57}N_5O_{10}S \cdot HCl$: C, 56.82; H, 7.09; N, 8.50; S, 3.89; Cl, 4.30. Found: C, 56.88; H, 6.98; N, 8.48; S, 3.99; Cl, 4.40.

Example 55 t-butoxycarbonyl-N$^\alpha$-ethyl-L-tyrosyl-D-methionylglycyl-N-(6-methoxy-6-oxohexyl)-L-phenylalaninamide monohydrochloride hemihydrate (SC-36821)

To a stirred mixture of 1.7 g (1.9 mmole) of the title product of Example 52 in 40 ml of methanol was added 10 ml of 10% aqueous potassium carbonate. After about 75 minutes the resultant solution was poured into a mixture of 150 ml of dichloromethane and 100 ml of 0.5M potassium bisulfate. The organic phase (containing the crude neutralized product) was separated and the aqueous layer was further extracted with dichloromethane. The combined organic layers were concentrated to dryness and purified by column chromatography, giving the analytically pure BOC-protected derivative of the title compound. [Analysis. Calcd. for $C_{39}H_{57}N_5O_9S$: C, 60.68; H, 7.44; N, 9.07; S, 4.15. Found: C, 60.64; H, 7.52; N, 8.90; S, 4.01.] The intermediate thus formed was converted to the title compound by the method described in Example 14. Structure Assignment was supported by elemental analysis.

Analysis. Calcd. for $C_{34}H_{49}N_5O_7S \cdot HCl \cdot \frac{1}{2}H_2O$: C, 56.93; H, 7.17; N, 9.77; S, 4.47; Cl, 4.94. Found: C, 56.98; H, 7.05; N, 9.82; S, 4.35; Cl, 5.11.

Example 56

N$^\alpha$-ethyl-L-tyrosyl-[4-(methylsulfinyl)-D-2-aminobutanoyl]glycyl-N-(6-methoxy-6-oxohexyl)-L-phenylalaninamide monohydrochloride hemihydrate (SC-36825)

The title compound was prepared by the method of Example 16 using the title product of Example 55. Structure assignment was supported by elemental analysis.

Analysis. Calcd. for $C_{34}H_{49}N_5O_8S\cdot HCl\cdot H_2O$: C, 55.68; H, 7.01; N, 9.55; S, 4.37; Cl, 4.83. Found: C, 55.44; H, 6.87; N, 9.47; S, 4.23; Cl, 4.99.

Example 57

O-(2-methylpropoxycarbonyl)-2,3,6-trimethyltyrosyl-D-methionylglycyl-N-(6-methoxy-6-oxohexyl)-L-phenylalaninamide monohydrochloride trihydrate (SC-36874)

Using t-butoxycarbonyl-2,3,6-trimethyltyrosine prepared from 2,3,5-trimethylphenol by the method of Example 12, the title compound was prepared by the methods of Examples 52 (basically the method of Example 13 without resolution of the racemic mixture) and 14. Structure assignment was supported by elemental analysis.

Analysis. Calcd. for $C_{40}H_{59}N_5O_9S\cdot HCl\cdot 3H_2O$: C, 54.81; H, 7.58; N, 7.99; S, 3.66; Cl, 4.04. Found: C, 54.87; H, 6.93; N, 8.07; S, 3.81; Cl, 4.12.

Example 58

O-(2-methylpropoxycarbonyl)-2,3,6-trimethyltyrosyl-[4-(methylsulfinyl)-D-2-aminobutanoyl]glycyl-N-(6-methoxy-6-oxohexyl)-L-phenylalaninamide monohydrochloride sesquihydrate (SC-36889)

The title compound was prepared by the method of Example 16 using the title product of example 57. Structure assignment was supported by elemental analysis.

Analysis. Calcd. for $C_{40}H_{59}N_5O_{10}S\cdot HCl\cdot 3/2H_2O$: C, 56.02; H, 7.40; N, 8.17; S, 3.74; Cl, 4.13. Found: C, 56.18; H, 7.14; N, 8.23; S, 3.80; Cl, 4.11.

Example 59

2,3,6-trimethyl-L-tyrosyl-D-methionylglycyl-N-(6-methoxy-6-oxohexyl)-L-phenylalaninamide monohydrochloride hemihydrate (SC-37279)

Using t-butoxycarbonyl-2,3,6-trimethyltyrosine prepared from 2,3,5-trimethylphenol by the method of Example 12, the title compound was prepared by the methods of Examples 52 (except that the racemic mixture was separated as in Example 13) and 55. Structure assignment was supported by elemental analysis.

$[\alpha]_D +23.3+$; $[\alpha]_{365} +100.0°$ (methanol)

Analysis. Calcd. for $C_{35}H_{51}N_5O_7S\cdot HCl\cdot\frac{1}{2}H_2O$: C, 57.48; H, 7.30; N, 9.58; S, 4.38; Cl, 4.85. Found: C, 57.13; H, 7.01; N, 9.50; S, 4.60; Cl, 5.10.

Example 60

2,3,6-trimethyl-D-tyrosyl-D-methionylglycyl-N-(6-methoxy-6-oxohexyl)-L-phenylalaninamide monohydrochloride hemihydrate (SC-37277)

The title compound was prepared by the methods summarized in Example 59, except for using the isomer having 2,3,6-trimethyl-D-tyrosine. Structure assignment was supported by elemental analysis.

$[\alpha]_D -49.8°$; $[\alpha]_{365} -186.5°$ (methanol)

Analysis. Calcd. for $C_{35}H_{51}N_5O_7S\cdot HCl\cdot\frac{1}{2}H_2O$: C, 57.48; H, 7.30; N, 9.58; S, 4.38; Cl, 4.85. Found: C, 57.13; H, 6.99; N, 9.49; S, 4.49; Cl, 5.10.

Example 61

2,3,6-trimethyl-L-tyrosyl-[4-methylsulfinyl)-D-2-aminobutanoyl]glycyl-N-(6-methoxy-6-oxohexyl)-L-phenylalaninamide monohydrochloride monohydrate (SC-37336)

The title compound was prepared by the method of Example 16 using the title product of Example 59. Structure assignment was supported by elemental analysis.

$[\alpha]_D +40.4°$; $[\alpha]_{365} +150.7°$ (methanol)

Analysis. Calcd. for $C_{35}H_{51}N_5O_8S\cdot HCl\cdot H_2O$: C, 55.58; H, 7.19; N, 9.26; S, 4.23; Cl, 4.69. Found: C, 55.60; H, 7.01; N, 9.26; S, 4.23; Cl, 4.86.

Example 62

2,3,6-trimethyl-D-tyrosyl-[4-methylsulfinyl)-D-2-aminobutanoyl]glycyl-N-(6-methoxy-6-oxo-hexyl)-L-phenylalaninamide monohydrochloride monohydrate (SC-37334)

The title compound was prepared by the method of Example 16 using the title product of Example 60. Structure assignment was supported by elemental analysis.

$[\alpha]_D -46.2°$; $[\alpha]_{365} -166.2°$ (methanol)

Analysis. Calcd. for $C_{35}H_{51}N_5O_8S\cdot HCl\cdot H_2O$: C, 55.58; H, 7.19; N, 9.26; S, 4.23; Cl, 4.69. Found: C, 55.98; H, 7.01; N, 9.19; S, 4.23; Cl, 5.14.

Example 63

O-(2-methylpropoxycarbonyl)-2-methyltyrosyl-D-methionylglycyl-N-(6-methoxy-6-oxohexyl)-L-phenylalaninamide monohydrochloride hemihydrate (SC-36886)

Using t-butoxycarbonyl-2-methyltyrosine prepared from 3-methylphenol by the method of Example 12, the title compound was prepared by the methods of Examples 52 (basically the method of Example 13 without resolution of the racemic mixture) and 14. Structure assignment was supported by elemental analysis.

Analysis. Calcd. for $C_{38}H_{55}N_5O_9S\cdot HCl\cdot\frac{1}{2}H_2O$: C, 56.80; H, 7.15; N, 8.71; S, 3.99; Cl, 4.41. Found: C, 56.80; H, 7.05; N, 8.82; S, 4.09; Cl, 4.47.

Example 64

O-(2-methylpropoxycarbonyl)-2-methyltyrosyl-[4-(methylsulfinyl)-D-2-aminobutanoyl]-glycyl-N-(6-methoxy-6-oxohexyl)-L-phenylalaninamide monohydrochloride hemihydrate (SC-36899)

The title compound was prepared by the method of Example 16 using the title product of Example 63. Structure assignment was supported by elemental analysis.

Analysis. Calcd. for $C_{38}H_{55}N_5O_{10}S\cdot HCl\cdot H_2O$: C, 55.69; H, 7.01; N, 8.55; S, 3.91; Cl, 4.33. Found: C, 55.53; H, 7.00; N, 8.73; S, 3.90; Cl, 4.39.

Example 65

2-methyl-L-tyrosyl-D-methionylglycyl-N-(6-methoxy-6-oxohexyl)-L-phenylalaninamide monohydrochloride Using t-butoxycarbonyl-2-methyltyrosine prepared from 3-methylphenol by the method of Example 12, the title compound is prepared by the methods of Examples 52 (except that the racemic mixture is separated as in Example 13) and 55.

Example 66

2-methyl-D-tyrosyl-D-methionylglycyl-N-(6-methoxy-6-oxohexyl)-L-phenylalaninamide monohydrochloride The title compound is prepared by the methods summarized in Example 65, except for using the isomer having 2-methyl-D-tyrosine.

Example 67

2-methyl-L-tyrosyl-[4-(methylsulfinyl)-D-2-aminobutanoyl]glycyl-N-(6-methoxy-6-oxohexyl)-L-phenylalaninamide monohydrochloride The title compound is prepared by the method of Example 16 using the title product of Example 65.

Example 68

2-methyl-D-tyrosyl-[4-(methylsulfinyl)-D-2-aminobutanoyl]glycyl-N-(6-methoxy-6-oxohexyl)-L-phenylalaninamide monohydrochloride The title compound is prepared by the method of Example 16 using the title product of Example 66.

Example 69

O-(2-methylpropoxycarbonyl)-3-t-butyl-tyrosyl-D-methionylglycyl-N-(6-methoxy-6-oxohexyl)-L-phenylalaninamide monohydrochloride (SC-36898)

Using t-butoxycarbonyl-3-t-butyltyrosine prepared from 2-t-butylphenol by the method of Example 12, the title compound was prepared by the methods of Examples 52 (basically the method of Example 13 without resolution of the racemic mixture) and 14. Structure assignment was supported by elemental analysis.

Analysis. Calcd. for $C_{41}H_{61}N_5O_9S \cdot HCl$: C, 58.87; H, 7.47; N, 8.37; S, 3.83; Cl, 4.24. Found: C, 58.53; H, 7.52; N, 8.35; S, 3.79; Cl, 4.24.

Example 70

O-(2-methylpropoxycarbonyl)-3-t-butyltyrosyl-[4-(methylsulfinyl)-D-2-aminobutanoyl]glycyl-N-(6-methoxy-6-oxohexyl)-L-phenylalaninamide monohydrochloride hemihydrate (SC-36933)

The title compound was prepared by the method of Example 16 using the title product of Example 69. Structure assignment was supported by elemental analysis.

Analysis. Calcd. for $C_{41}H_{61}N_5O_{10}S \cdot HCl \cdot \frac{1}{2}H_2O$: C, 57.16; H, 7.37; N, 8.13; S, 3.72; Cl, 4.11. Found: C, 57.12; H, 7.36; N, 8.13; S, 3.68; Cl, 3.98.

Example 71

3-t-butyl-L-tyrosyl-D-methionylglycyl-N-(6-methoxy-6-oxohexyl)-L-phenylalaninamide monohydrochloride (SC-39926)

Using t-butoxycarbonyl-3-t-butyltyrosine prepared from 2-t-butylphenol by the method of Example 12, the title compound was prepared by the methods of Examples 52 (except that the racemic mixture was separated as in Example 13) and 55. Structure assignment was supported by elemental analysis.

$[\alpha]_D +6.8°$; $[\alpha]_{365} +27.5°$ (methanol)

Analysis. Calcd. for $C_{36}H_{53}N_5O_7S \cdot HCl$: C, 58.72; H, 7.39; N, 9.51. Found: C, 58.58; H, 7.39; N, 9.30.

Example 72

3-t-butyl-D-tyrosyl-D-methionylglycyl-N-(6-methoxy-6-oxohexyl)-L-phenylalaninamide monohydrochloride (SC-39913)

The title compound was prepared by the methods summarized in Example 52, except for using the isomer having 3-t-butyl-D-tyrosine. Structure assignment was supported by elemental analysis.

$[\alpha]_D -19.4°$; $[\alpha]_{365} -92.3°$ (methanol)

Analysis. Calcd. for $C_{36}H_{53}N_5O_7S \cdot HCl$: C, 58.72; H, 7.39; N, 9.51; S, 4.35. Found: C, 58.47; H, 7.42; N, 9.52; S, 4.35.

Example 73

3-t-butyl-L-tyrosyl-[4-(methylsulfonyl)-D-2-aminobutanoyl]glycyl-N-(6-methoxy-6-oxohexyl)-L-phenylalaninamide monohydrochloride hemihydrate (SC-39983)

The title sulfone was prepared from the title product of Example 71 using the method of Example 16, except that the methanolic hydrogen peroxide solution was heated at reflux for about one hour. Structure assignment was supported by elemental analysis.

$[\alpha]_D +14.2°$; $[\alpha]_{365} +60.4°$ (methanol)

Analysis. Calcd. for $C_{36}H_{53}N_5O_9S \cdot HCl \cdot \frac{1}{2}H_2O$: C, 55.62; H, 7.13; N, 9.01. Found: C, 55.38; H, 7.29; N, 9.03.

Example 74

3-t-butyl-D-tyrosyl-[4-(methylsulfonyl)-D-2-aminobutanoyl]glycyl-N-(6-methoxy-6-oxohexyl)-L-phenylalaninamide monohydrochloride hemihydrate (SC-39967)

The title compound was prepared by the method of Example 73 using the title product of Example 72. Structure assignment was supported by elemental analysis.

$[\alpha]_D -16.0°$; $[\alpha]_{365} -64.9°$ (methanol)

Analysis. Calcd. for $C_{36}H_{53}N_5O_9S \cdot HCl \cdot \frac{1}{2}H_2O$: C, 55.62; H, 7.13; N, 9.01. Found: C, 55.20; H, 7.21; N, 9.00.

Example 75

2,4-dimethyl-3-(2-methylpropoxycarbonyloxy)-phenylalanyl-D-methionylglycyl-N-(6-methoxy-6-oxohexyl)-L-phenylalaninamide monohydrochloride hemihydrate (SC-36888)

Using t-butoxycarbonyl-2,4-dimethyl-3-hydroxyphenylalanine prepared from 2,6-dimethylphenol by the method of Example 12, the title compound was prepared by the methods of Examples 52 (basically the method of Example 13 without the resolution of the racemic mixture) and 14. Structure assignment was supported by elemental analysis.

Analysis. Calcd. for $C_{39}H_{57}N_5O_9S \cdot HCl \cdot \frac{1}{2}H_2O$: C, 57.30; H, 7.27; N, 8.57; S, 3.92; Cl, 4.34. Found: C, 57.30; H, 7.18; N, 8.57; S, 3.96; Cl, 4.30.

Example 76

2,4-dimethyl-3-(2-methylpropoxycarbonyloxy)-phenylalanyl-[4-(methylsulfinyl)-D-2-aminobutanoyl]glycyl-N-(6-methoxy-6-oxohexyl)-L-phenylalaninamide monohydrochloride hemihydrate (SC-36917)

The title compound was prepared by the method of Example 16 using the title product of example 75. Structure assignment was supported by elemental analysis.

Analysis. Calcd. for $C_{39}H_{57}N_5O_{10}S \cdot HCl \cdot 2H_2O$: C, 54.44; H, 7.26; N, 8.14; S, 3.73; Cl, 4.12. Found: C, 54.38; H, 6.77; N, 8.14; S, 3.78; Cl, 4.12.

Example 77

2,4-dimethyl-3-hydroxyphenylalanyl-D-methionylglycyl-N-(6-methoxy-6-oxohexyl)-L-phenylalaninamide monohydrochloride hemihydrate (SC-40367)

Using t-butoxycarbonyl-2,4-dimethyl-3-hydroxyphenylalanine prepared from 2,6-dimethylphenol by the method of Example 12, the title compound was prepared by the methods of Examples 52 (without the resolution of the racemic mixture) and 55. Structure assignment was supported by elemental analysis.

Analysis. Calcd. for $C_{33}H_{49}N_5O_8S \cdot HCl \cdot \tfrac{1}{2}H_2O$: C, 54.94; H, 7.13; N, 9.71. Found: C, 54.84; H, 6.66; N, 9.26.

Example 78

2,6-dimethyl-L-tyrosyl-D-alanylglycyl-N-(6-methoxy-6-oxohexyl)-L-phenylalanamide monohydrochloride (SC-39865)

The title compound was prepared by the methods of Examples 8 (except for using t-butoxycarbonyl-D-alanine instead of t-butoxycarbonyl-D-methionine), 9, 10, 11, 13 and 14. Structure assignment was supported by elemental analysis.

$[\alpha]_D + 53.9°$; $[\alpha]_{365} + 200°$ (methanol)

Analysis. Calcd. for $C_{32}H_{45}N_5O_7 \cdot HCl$: C, 59.20; H, 7.30; N, 10.79. Found: C, 58.83; H, 7.14; N, 10.53.

Example 79

2,6-dimethyl-D-tyrosyl-D-alanylglycyl-N-(6-methoxy-6-oxohexyl)-L-phenylalanamide monohydrochloride hemihydrate (SC-39804)

The title compound was prepared by the methods summarized in Example 78, except for using the method of Example 15 instead of Example 14. Structure assignment was supported by elemental analysis.

$[\alpha]_D - 33.3°$; $[\alpha]_{365} - 122.2°$ (methanol)

Analysis. Calcd. for $C_{32}H_{45}N_5O_7 \cdot HCl \cdot \tfrac{1}{2}H_2O$: C, 58.48; H, 7.21; N, 10.66. Found: C, 58.45; H, 7.18; N, 10.56.

Example 80

Renin Inhibition Activity

The results of renin inhibition activity (human renin test) with respect to certain of the preferred embodiments of the compounds of Formula I are set forth in Table I following.

TABLE I

| Compound Example No. | % Inhibition |
|---|---|
| 58 | 26 |
| 63 | 23 |
| 64 | 22 |
| 69 | 43 |
| 70 | 25 |
| 73 | 21 |
| 74 | 28 |
| 77 | 73 |

CHART A

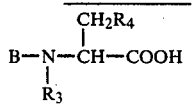

XI

CHART A -continued

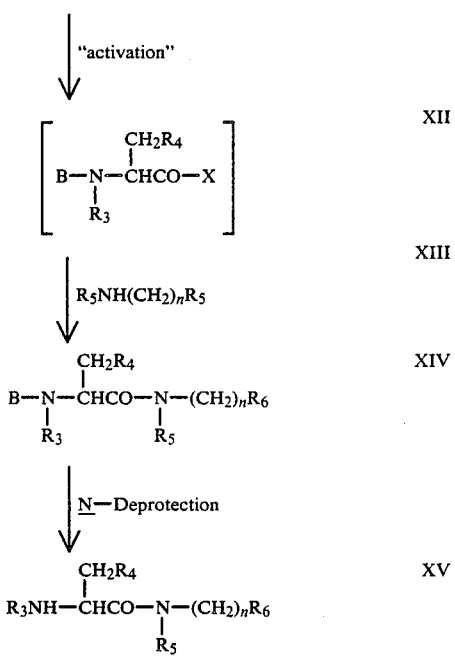

CHART B

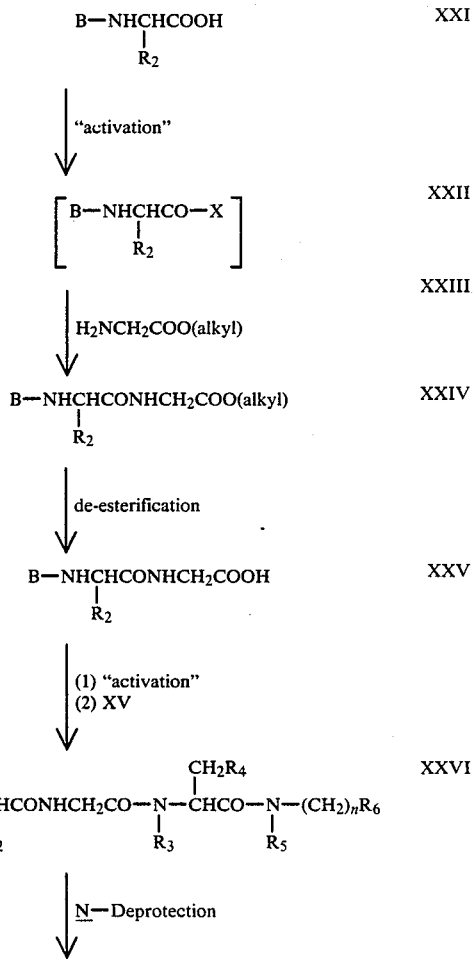

-continued
CHART B

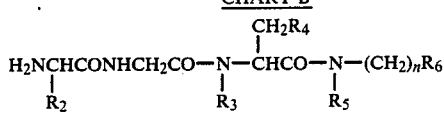
XXVII

CHART C

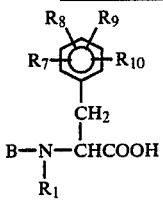

(1) "activation"
(2) XXVII

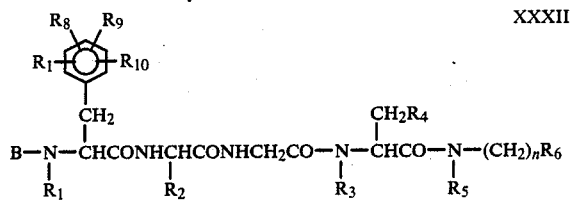
XXXII

Deprotection

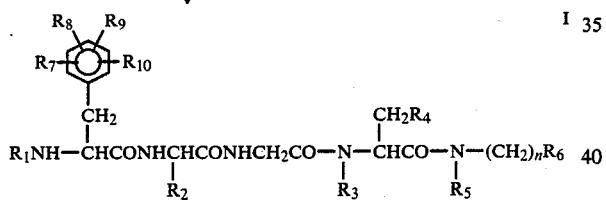
I

CHART D

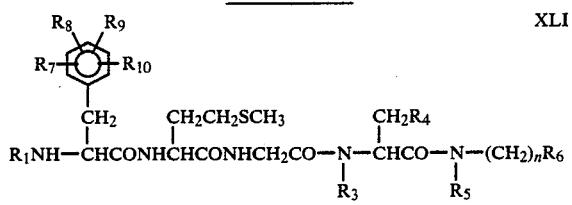
XLI

H₂O₂

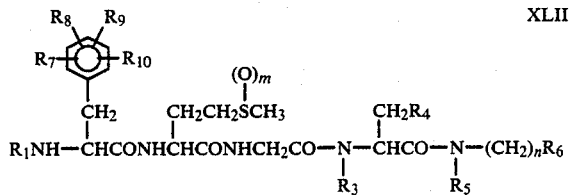
XLII

What is claimed is:

1. A method of promoting an antihypertensive effect in an animal in need thereof comprising administering thereto an antihypertensively effective amount of a compound of the formula

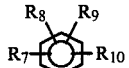
XXXI or pharmaceutically acceptable salts thereof wherein R₁ is:
(a) hydrogen; or
(b) alkyl of 1 to 6 carbon atoms, inclusive;
wherein R₂ is:
(a) alkyl of 1 to 6 carbon atoms, inclusive; or
(b)

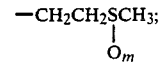

m being either zero, 1 or 2;
wherein R₃ is:
(a) hydrogen; or
(b) alkyl of 1 or 2 carbon atoms, inclusive;
wherein R₄ is:
(a) phenyl, phenyl substituted by alkyl of from 1 to 6 carbon atoms, inclusive; or
wherein R₅ is:
(a) hydrogen; or
(b) alkyl of 1 to 6 carbon atoms, inclusive;
wherein R₆ is:
(a) carboxy;
(b) alkoxycarbonyl of 2 to 7 carbon atoms, inclusive;
(c) CONH₂;
(d) N,N-dialkylcarbamoyl of 3 to 7 carbon atoms, inclusive;
(e) hydroxy; or
(f) alkanoyloxy of 2 to 7 carbon atoms, inclusive;
wherein R₇, R₈, and R₉ are H or alkyl of 1 to 6 carbon atoms, and wherein R₇, R₈ and R₉ are the same or different;
wherein R₁₀ is:
(a) hydrogen;
(b) hydroxy; or
(c) alkoxycarbonyloxy wherein the alkoxy portion is from 1 to 6 carbon atoms, inclusive;
wherein n is an integer of from 3 to 10 inclusive and the pharmacologically acceptable acid addition salts thereof.

2. A method according to claim 1 wherein R₆ is alkoxycarbonyl of 2 to 7 carbon atoms.

3. A method according to claim 1 wherein R₁ is hydrogen.

4. A method according to claim 1 wherein R₂ is

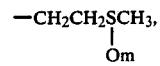

m being 0, 1, or 2.

5. A method according to claim 4 wherein m is 1 or 2.

6. A method according to claim 1 wherein R₃ is hydrogen.

7. A method according to claim 1 wherein $R_5$ is hydrogen.

8. A method according to claim 1 wherein $R_7$, $R_8$, and $R_9$ are H or alkyl of 1 to 6 carbon atoms, and may be the same or different and $R_{10}$ is hydroxy.

9. A method according to claim 8 wherein two of $R_7$, $R_8$, and $R_9$ are alkyl of 1 to 6 carbon atoms and the other is hydrogen.

10. A method according to claim 1 wherein $R_4$ is phenyl.

11. A method according to claim 1 wherein said compound is selected from O-(2-methylpropoxycarbonyl)-2,3,6-trimethyltyrosyl-[4-(methylsulfinyl)-D-2-aminobutanoyl]glycyl-N-(6-methoxy-6-oxohexyl)-L-phenylalaninamide monohydrochloride, O-(2-methylpropoxycarbonyl)-2-methyltyrosyl-D-methionylglycyl-N-(6-methoxy-6-oxohexyl)-L-phenylalaninamide monohydrochloride, O-(2-methylpropoxycarbonyl)-2-methyltyrosyl-[4-(methylsulfinyl)-D-2-aminobutanoyl]-glycyl-N-(6-methoxy-6-oxohexyl)-L-phenylalaninamide monohydrochloride, O-(2-methylpropoxycarbonyl)-3-t-butyl-1-tyrosyl-D-methionylglycyl-N-(6-methoxy-6-oxohexyl)-L-phenylalaninamide monohydrochloride, O-(2-methylpropoxycarbonyl)-3-t-butyltyrosyl-[4-(methylsulfinyl)-D-2-aminobutanoyl]glycyl-N-(6-methoxy-6-oxohexyl)-L-phenylalaninamide monohydrochloride, 3-t-butyl-L-tyrosyl-[4-(methylsulfonyl)-D-2-aminobutanoyl]glycyl-N-(6-methoxy-6-oxohexyl)-L-phenylalaninamide monohydrochloride, 3-t-butyl-D-tyrosyl-[4-(methylsulfonyl)-D-2-aminobutanoyl]glycyl-N-(6-methoxy-6-oxo-hexyl)-L-phenylalaninamide monohydrochloride, 2,4-dimethyl-3-hydroxyphenylalanyl-D-methionyl-glycyl-N-(6-methoxy-6-oxohexyl)-L-phenylalaninamide monohydrochloride.

12. A method according to claim 11 wherein said compound is 2,4-dimethyl-3-hydroxyphenylalanyl-D-methionyl-glycyl-N-(6-methoxy-6-oxohexyl)-L-phenylalaninamide monohydrochloride.

13. A method according to claim 12, wherein said compound is administered in combination with a non-toxic pharmaceutically acceptable carrier.

14. A method according to claim 13, wherein said compound is administered orally.

* * * * *